United States Patent
Park et al.

(10) Patent No.: US 10,736,944 B2
(45) Date of Patent: Aug. 11, 2020

(54) COMPOSITIONS FOR PREVENTING OR TREATING SEPSIS OR SEPTIC SHOCK COMPROMISING ADK PROTEIN AS ACTIVE INGREDIENT

(71) Applicant: KONKUK UNIVERSITY GLOCAL INDUSTRY-ACADEMIC COLLABORATION FOUNDATION, Gwangjin-gu, Seoul (KR)

(72) Inventors: Yeong Min Park, Seoul (KR); In Duk Jung, Seoul (KR); Sung Jae Shin, Seoul (KR); Jung Hee Park, Iksan-si (KR); Seung Jun Lee, Yeongju-si Gyeongsangbuk-do (KR); Tae Heung Kang, Buk-gu Gwangju (KR); Byoung Yul Soh, Namwon-si Jeollabuk-do (KR)

(73) Assignee: KONKUK UNIVERSITY GLOCAL INDUSTRY-ACADEMIC COLLABORATION FOUNDATION (KR)

(*) Notice: Subject to any disclaimer, the term of this patent is extended or adjusted under 35 U.S.C. 154(b) by 0 days.

(21) Appl. No.: 16/120,603

(22) Filed: Sep. 4, 2018

(65) Prior Publication Data

US 2019/0060418 A1 Feb. 28, 2019

Related U.S. Application Data

(63) Continuation of application No. 14/414,366, filed as application No. PCT/KR2014/006028 on Jul. 7, 2014, now abandoned.

(30) Foreign Application Priority Data

Apr. 23, 2014 (KR) .................. 10-2014-0048573

(51) Int. Cl.
*A61K 38/45* (2006.01)
*A23L 29/00* (2016.01)

(52) U.S. Cl.
CPC .............. *A61K 38/45* (2013.01); *A23L 29/06* (2016.08); *A23V 2002/00* (2013.01); *C12Y 207/0102* (2013.01)

(58) Field of Classification Search
CPC ..... A61K 38/45; A23L 29/06; A23V 2002/00; C12Y 207/0102
USPC ......................................... 424/94.5
See application file for complete search history.

(56) References Cited

FOREIGN PATENT DOCUMENTS

| WO | 2002077183 | 10/2002 |
| WO | 2008124647 | 10/2008 |

OTHER PUBLICATIONS

Boison, "Adenosine Kinase: Exploitation for Therapeutic Gain," Pharmacol Rev. Apr. 16, 2013;65(3):906-43.
Bridges et al., "Severe Tuberculosis Sepsis in an Immunocompetent Patient," Am J Med. Mar. 2006;119(3):e11-e14.
Chong, Sepsis and Septic Shock, Available online at: www.columbia.edu/itc/hs/medical/pathophys/id/2009/sepsisNotes.pdf, Created Aug. 17, 2009, 14 pages.
Marco Bellinzoni et al., "The crystal structure of *Mycobacterium tuberculosis* adenylate kinase in complex with two molecules of ADP and Mg2+ supports an associative mechanism for phosphoryl transfer," Protein Sci. Jun. 2006; 15(6): 1489-1493.
Moura-Alves et al., "AhR sensing of bacterial pigments regulates antibacterial defence," Nature. Aug. 28, 2014;512(7515):387-92.
Munier-Lehmann et al., "A new subfamily of short bacterial adenylate kinases with the *Mycobacterium tuberculosis* enzyme as a model: A predictive and experimental study." Proteins Aug. 1999;36(2):238-48.
Peng Y. et al., "Angiogenesis Inhibitor Endostatin Protects Mice with Sepsis from Multiple Organ Dysfunction Syndrome," Shock. 2015, pp. 357-364.

*Primary Examiner* — Jennifer M. H. Tichy
(74) *Attorney, Agent, or Firm* — Riverside Law LLP (57) ABSTRACT

The present invention relates to a composition for preventing or treating sepsis or septic shock including a *Mycobacterium tuberculosis*-derived adenosine kinase (ADK) protein as an active ingredient. The *Mycobacterium tuberculosis*-derived ADK protein according to one exemplary embodiment of the present invention has an effect of inhibit binding between the LPS and cells by binding to LPS, and also has an excellent therapeutic effect against sepsis by enhancing viability in a sepsis animal model and suppressing inflammatory response in the lung and cell death in the spleen.

4 Claims, 10 Drawing Sheets

Specification includes a Sequence Listing.

COMPOSITIONS FOR PREVENTING OR TREATING SEPSIS OR SEPTIC SHOCK COMPROMISING ADK PROTEIN AS ACTIVE INGREDIENT

CROSS-REFERENCE TO RELATED APPLICATIONS

This application is a continuation of U.S. patent application Ser. No. 14/414,366, filed Jan. 12, 2015, which is the U.S. national phase application filed under 35 U.S.C. § 371 claiming benefit to PCT International Patent Application No. PCT/KR14/06028, filed Jul. 7, 2014, which claims priority to Korean Patent Application No. 10-2014-0048573, filed Apr. 23, 2014, the disclosure of which is incorporated herein by reference in its entirety.

TECHNICAL FIELD

The present invention relates to a composition for preventing or treating sepsis or septic shock including an adenosine kinase (ADK) protein derived from *Mycobacterium tuberculosis* as an active ingredient.

BACKGROUND ART

Sepsis is an inflammatory response induced as a lipopolysaccharide (LPS) that is an ingredient of a cell wall acts as a toxin to activate the immune system in a living body excessively when the living body is infected with pathogenic gram-negative bacteria, and causes infections throughout the whole body or is often accompanied by shock when its symptoms are severe. Specifically, the sepsis often develops when hosts who are low resistant to humoral immunodeficiency or cellular immunodeficiency, such as patients, the aged, or premature babies who suffer from basal diseases such as malignant tumors, leukemia, malignant lymphoma, acquired immunodeficiency syndromes (AIDSs), collagen diseases, renal failure, liver diseases, cerebrovascular disorders, diabetes, and the like, undergo treatment and surgery such as chemiotherapy using adrenal steroids or anti-tumor agents, radiotherapy referred to as cobalt radiation, or indwelling catheter, blood dialysis, organ transplantation, heart surgery, and the like. Sepsis is a primary cause of death of hospital patients in the intensive care unit (ICU), and is a very serious disease since its mortality usually amounts to 30% or more. In spite of the development of medical technology, the patients are often infected from the aftereffect following the surgery, and still develop sepsis all over the world. Also, when peoples, such as newborn infants or the aged, which have weaker immune systems in the body, become infected, they often develop into sepsis. As one representative example, mature infants are known to develop neonatal sepsis at a rate of 3/1,000 cases, and premature babies are known to have an incidence rate 3 to 4 times higher than the mature infants. When a patient suffers from sepsis, the patient is generally treated with an antibiotic. However, when pathogens grow highly due to the delay of proper treatment or when a patient is infected with a strain strongly resistant to the antibiotic, the effective treatment cannot be achieved using only the antibiotic. With regard to a gradual increase in pathogens resistant to various antibiotics, the treatment of sepsis or septic shock has emerged as a very important issue. However, a proper therapeutic agent for treating sepsis or septic shock remains to be developed.

The present inventors have made intensive studies to meet the above-described requirements, and found that an ADK protein derived from *Mycobacterium tuberculosis* binds to LPS to show an excellent therapeutic effect against sepsis. Therefore, the present invention has been completed, based on these facts.

DISCLOSURE

Technical Problem

The present invention has been proposed to solve the above drawbacks, and an object of the present invention is to provide a pharmaceutical composition for preventing or treating sepsis or septic shock including an adenosine kinase (ADK) protein as an active ingredient.

Also, another object of the present invention is to provide a food composition for preventing or improving sepsis or septic shock including an ADK protein as an active ingredient.

Technical Solution

In order to achieve the above objects, a pharmaceutical composition for preventing or treating sepsis or septic shock including an ADK protein as an active ingredient is provided.

Also, a food composition for preventing or improving sepsis or septic shock including an ADK protein as an active ingredient is provided.

Advantageous Effects

The *Mycobacterium tuberculosis*-derived ADK protein according to one exemplary embodiment of the present invention has an inhibitory effect on binding between the LPS and cells by binding to LPS, and has an excellent therapeutic effect against sepsis or septic shock by enhancing viability in a sepsis animal model and suppressing inflammatory response in the lung and cell death in the spleen.

BEST MODE

The present invention provides a composition for preventing or treating sepsis or septic shock including an adenosine kinase (ADK) protein as an active ingredient.

Here, the composition includes a pharmaceutical composition, and a food composition.

Hereinafter, the present invention will be described in further detail.

The ADK protein is derived from *Mycobacterium tuberculosis*, and preferably includes a protein having an amino acid sequence set forth in SEQ ID NO: 1, or a protein encoded by a DNA sequence set forth in SEQ ID NO: 2, and a functional equivalent thereof. In the present invention, the term "functional equivalent" refers to a protein which has at least a sequence homology of at least 70% or more, preferably 80% or more, more preferably 90% or more, and further preferably 95% or more with the amino acid sequence set forth in SEQ ID NO: 1 due to the addition, substitution or deletion of an amino acid(s), and thus shows substantially the same bioactivity as the protein having the amino acid sequence set forth in SEQ ID NO: 1 or the protein encoded by the DNA sequence set forth in SEQ ID NO: 2.

The ADK protein according to one exemplary embodiment of the present invention includes a protein having the same amino acid sequence as its wild-type amino acid sequence, and amino acid sequence variants thereof, all of which also fall within the scope of the present invention. The term "variant" of the ADK protein refers to a protein having a different amino acid sequence from the wild-type amino acid sequence of the ADK protein due to the deletion, insertion, non-conservative or conservative substitution of one or more amino acid residues, or combinations thereof. The replacement of amino acids in a protein and a peptide, which does not generally alter the activities of molecules, is known in the related art. The ADK protein or variants thereof may be extracted or synthesized in the nature (Merrifleld, J. Amer. chem. Soc. 85: 2149-2156, 1963), or may be prepared based on the DNA sequence using a genetic recombination method (Sambrook et al, Molecular Cloning, Cold Spring Harbour Laboratory Press, New York, USA, Version 2, 1989).

In the present invention, the "sepsis" refers to a condition in which a patient is infected with a microorganism to show serious inflammatory response in the whole body. When a patient has two or more symptoms selected from the group consisting of fever symptoms in which the body temperature increases to 38° or higher, or hypothermia in which the body temperature decreases to 36° or less, an increase in breathing rate of 24 per minute (tachypnea), a heart rate of 90 or more per minute (pyknocardia), and an increase or remarkable decrease in leukocyte counts in a blood test, this condition is referred to as a systemic inflammatory response syndrome (SIRS). Such an SIRS is referred to as sepsis when the SIRS is caused by the infection of the microorganism. In the body, pathogens in an infected lesion continuously or intermittently enter the bloodstream, colonize various organs or tissues to develop lesions and cause serious constitutional symptoms. A causative organism includes *Staphylococcus* sp., *Streptococcus* sp., *Escherichia coli*, *Pseudomonas aeruginosa*, *Mycobacterium tuberculosis*, *Klebsiella pneumoniae*, eumycetes, anaerobic bacteria, and the like.

The *Mycobacterium tuberculosis*-derived ADK protein according to one exemplary embodiment of the present invention has an effect of inhibit binding between the LPS and cells by binding to LPS, and has an excellent therapeutic effect against sepsis or septic shock by enhancing viability in a sepsis animal model and suppressing inflammatory response in the lung and cell death in the spleen.

Therefore, the ADK protein according to one exemplary embodiment of the present invention may be effectively used for medical supplies and health functional foods for preventing or treating sepsis or septic shock.

The composition according to one exemplary embodiment of the present invention may further include a proper carrier, excipient, and diluent, which are generally used to prepare pharmaceutical compositions. The pharmaceutical composition according to one exemplary embodiment of the present invention may be formulated in the form of oral formulations such as powders, granules, tablets, capsules, suspensions, emulsions, syrup, or aerosols, preparations for external use, suppositories, and sterile injectable solutions, and used according to conventional related methods. Suitable preparations known in the related art are preferably those disclosed in Remington's Pharmaceutical Science, Mack Publishing Company, Easton Pa.

The carrier, excipient and diluent that may be included in the pharmaceutical composition according to one exemplary embodiment of the present invention may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oils. When formulated, the pharmaceutical composition is prepared using a widely used diluent or excipient such as a filler, a bulking agent, a binding agent, a wetting agent, a disintegrating agent, or a surfactant. Solid preparations for oral administration encompass tablets, pills, powders, granules, capsules, and the like. Such a solid preparation may be prepared by mixing at least one excipient, for example, starch, calcium carbonate, sucrose, lactose, or gelatin, with the active ingredient. Also, lubricating agents such as magnesium stearate, talc, and the like are used in addition to the simple excipients. Liquid preparations for oral administration encompass suspensions, liquids for internal use, emulsions, syrup, and the like. In addition to widely used simple diluents such as water and liquid paraffin, various excipients, for example, a wetting agent, a sweetening agent, an air freshener, a preservative, and the like, may be included in the composition. Preparations for parenteral administration encompass a sterile aqueous solution, a non-aqueous solvent, a suspension, an emulsion, a lyophilized preparation, and a suppository. Vegetable oils such as propylene glycol, polyethylene glycol, and olive oil, and injectable esters such as ethyl oleate may be used as the non-aqueous solvent and the suspension. Witepsol, Macrogol, Tween 61, Cacao butter, Laurin butter, glycerogelatine, and the like may be used as a base for suppositories.

The term "administration" or "administering" used herein means that a predetermined amount of the composition according to one exemplary embodiment of the present invention is provided to a subject using any proper methods.

A preferred dose of the pharmaceutical composition according to one exemplary embodiment of the present invention varies according to the condition and body weight of a subject, the severity of a disease, the type of a drug, a route for administration, and an administration time, but may be properly chosen by those skilled in the related art. For desirable effects, the composition according to one exemplary embodiment of the present invention may be administered daily at a dose of 0.001 to 1,000 mg/kg. In this case, the composition may be administered once a day, or administered in divided doses. In any aspects, the dose of the composition is not intended to limit the scope of the present invention. For example, the dose of the composition may be determined according to the type and severity of a disease in a subject, the activity of a drug, the sensitivity to the drug, an administration time, a route for administration, an excretion rate, the treatment duration, elements including drugs used together, and other factors widely known in the field of medicine.

The pharmaceutical composition according to one exemplary embodiment of the present invention may be administered to a subject via various routes. All kinds of administration modes may be possible expected. For example, the pharmaceutical composition may be administered orally, rectally, or intravenously, or administered by means of, intramuscular, subcutaneous, intracervical, or intracerebroventricular injection. Upon oral administration, however, oral compositions may be preferably formulated to coat an active drug or protect the active drug from being digested in the stomach since the proteins are digested. Preferably, the oral compositions may be administered in the form of an injection.

The pharmaceutical composition according to one exemplary embodiment of the present invention may further include at least one drug selected from the group consisting of a bronchodilator, an anti-histaminic agent, an anti-inflammatory analgesic agent, and an antibiotic.

For example, the bronchodilator that may be used herein may include a β-agonist, an anti-cholinergic agent, a methylxanthine, and the like, the anti-histaminic agent that may be used herein may include acrivastine, cetirizine, desloratadine, fexofenadine, levocertirizine, loratadine, mizolastine, ailmemazine, chlocertirizine, clemastine, cyproheptadine, hydroxyzine, ketotifen, promenthazine, and the like, the anti-inflammatory analgesic agent that may be used herein may include aspirin, diclofenac, fenoprofen, flurbiprofen, ibuprofen, indomethacin, ketoprofen, naproxen, piroxicam, sulindac, celecoxib, valdecoxib, rofecoxib, and the like, and the antibiotic that may be used herein may include a cephalosporin-based antibiotic, a phenicillin-based antibiotic, a quinolone-based antibiotic, an aminoglycoside-based antibiotic, a β-lactam-based antibiotic, and the like.

In the present invention, the term "health functional food" refers to a group of foods in which a food is endowed with higher added values to affect and express the functions of the corresponding food according to a certain purpose using physical, biochemical, biotechnological techniques, or refers to a food which is designed and processed to sufficiently express the body modulating functions, which are associated with the control of biological defense rhythms of food compositions, and the prevention of and recovery from diseases.

The health functional food may include a cytologically available food supplement, and may further include a proper carrier, excipient, and diluent, which are generally used to prepare health functional foods.

When the composition according to one exemplary embodiment of the present invention is used as the food supplement, the composition may be added per se, or used together with other foods or food ingredients. In this case, the composition may be properly used according to conventional methods. An amount of the mixed active ingredient may be properly determined according to a purpose of use (prophylaxis, health, or therapeutic treatment). Upon preparation of foods or drinks, the composition according to one exemplary embodiment of the present invention is generally added at a content of 15% by weight or less, preferably 10% by weight or less, based on the total amount of the ingredients. However, when the composition is ingested for a long period of time for the purpose of health and hygiene or health control, the dose of the composition may fall within this range. Also, the active ingredient may be used at a dose exceeding this range since the active ingredient has no problem in an aspect of safety.

In addition, the composition according to one exemplary embodiment of the present invention may include various nutrients, vitamins, electrolytes, a flavoring agent, a coloring agent, pectic acid and salts thereof, alginic acid and salts thereof, an organic acid, a protective colloid thickening agent, a pH adjuster, a stabilizing agent, a preservative, glycerin, alcohol, and a carbonating agent used in carbonated drinks. Further, the composition according to one exemplary embodiment of the present invention may include flesh for preparing a natural fruit juice, a fruit juice drink, and a vegetable-based juice. Such an ingredient may be used alone or in combination. Generally, the ratio of such an additive is of no great importance, but may be selected within a range of 0.01 to 0.1 parts by weight, based on 100 parts by weight of the composition according to one exemplary embodiment of the present invention.

MODE FOR INVENTION

Hereinafter, preferred Examples the present invention will be described in further detail. However, it should be understood that the detailed description provided herein is merely intended to provide a better understanding of the present invention, but is not intended to limit the scope of the present invention.

Example 1: Isolation of Dendritic Cells and Cloning of Recombinant ADK

1.1 Isolation and Induction of Dendritic Cells

Femoral bone marrow was extracted from 6- to 8-week old C57BL/6 mice using a syringe configured to extract a bone marrow. The extracted bone marrow was washed, and red blood cells were then removed with ammonium chloride. The isolated cells were cultured at 37° C. for 8 days under a 5% $CO_2$ atmosphere in a 6-well plate whose wells contained an RPMI 1640 medium (supplemented with 10% fetal bovine serum (FBS), 2 mM L-glutamine, 100 U/ml penicillin/streptomycin, 50 μM mercaptoethanol, 0.1 mM non-essential amino acids, 1 mM sodium pyruvate, 20 ng/ml GM-CSF, and 20 ng/ml IL-4). GM-CSF and IL-4 were used to induce differentiation of the cells into dendritic cells.

1.2 Cloning of Recombinant ADK (Rv0733)

Figure 1:
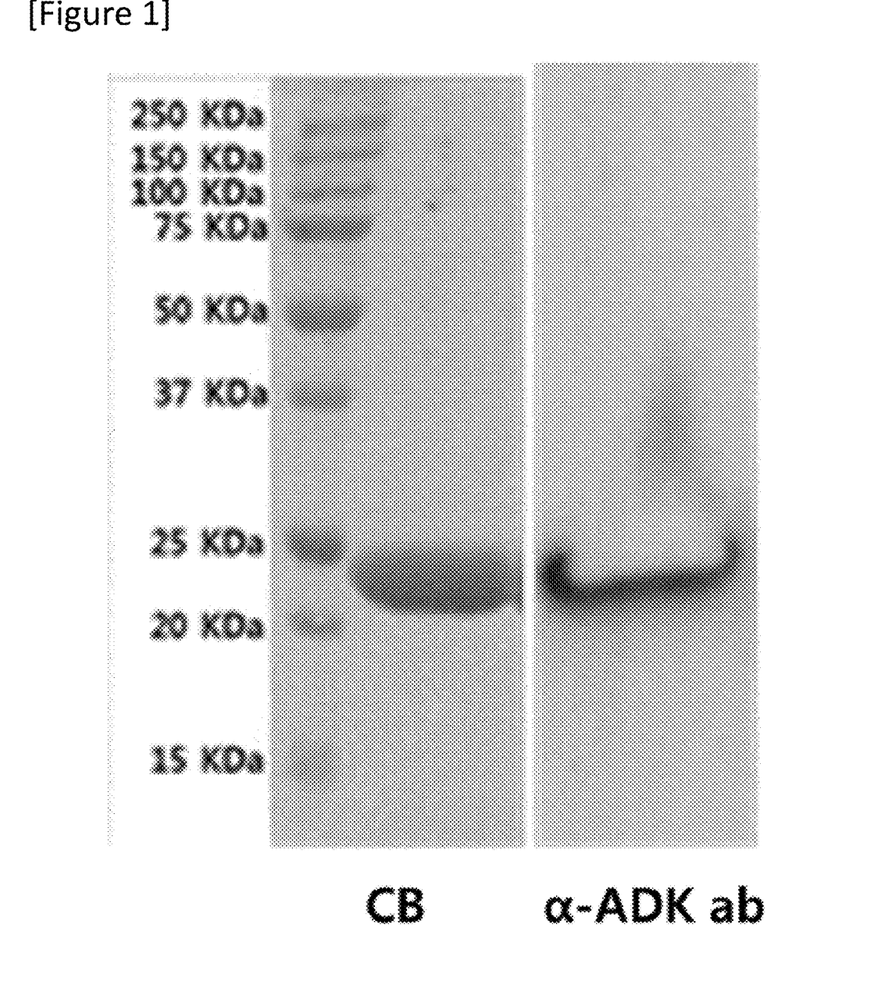
FIG. 1 is a diagram showing the results obtained by analyzing a recombinant ADK protein using sodium dodecyl sulfate polyacrylamide gel electrophoresis (SDS-PAGE) according to one exemplary embodiment of the present invention.

An ADK (Rv0733) region was amplified by a polymerase chain reaction (PCR) using the genomic DNA of *Mycobacterium tuberculosis* as a template (primers: 5'-CATATGAGAGTTTTGTTGCTGGGACCG-3' and 5'-AAGCTTCTTTCCCAGAGCCCGCAACGC-3'). The isolated PCR products were digested with restriction enzymes NdeI and HindIII, and inserted into an expression vector pET-28a. *E. coli* BL21 transformed with the pET-28a vector which was inserted the ADK gene was cultured at 37° C. for 12 hours in an LB medium (supplemented with 100 μg/ml ampicillin). Thereafter, 1 mM isopropyl-D-thiogalactopyranoside (IPTG) was added to the medium, and the *E. coli* BL21 was then cultured 6 hours, and lysed in a lysis buffer (supplemented with 1 M DTT, a lysozyme, and PMSF). The recombinant protein was purified using a nickel-nitrilotriacetic acid (Ni-NTA; Invitrogen, Carlsbad, Calif., USA) agarose according to the manufacturer's method. Finally, the purified recombinant ADK protein was analyzed to confirm through SDS-PAGE. The results are shown in FIG. 1.

Example 2: Analysis of Expression of Surface Molecules by ADK in Dendritic Cells To determine an effect of ADK on expression of surface molecules in dendritic cells, this experiment was performed, as follows. Dendritic cells were treated respectively with ADK at concentrations of 1, 5 or 10 μg/ml or LPS at concentrations of 50 ng/ml for 24 hours, and then recovered. LPS was a substance known to promote the maturation of dendritic cells. To analyze the expression of the surface molecules in the dendritic cells, the dendritic cells were stained with cell surface molecule-specific antibodies such as anti-CD11c-FITC, anti-CD80-PE, anti-CD86-PE, anti-MHC I-PE, and anti-MHC II-PE antibodies for 30 minutes, and then washed with PBS. The stained dendritic cells were fixed in 4% paraformaldehyde, and analyzed using a flow cytometer FACSCalibur (Becton Dickinson, San Jose, Calif.). The results are shown in FIG. 2.

Figure 2:
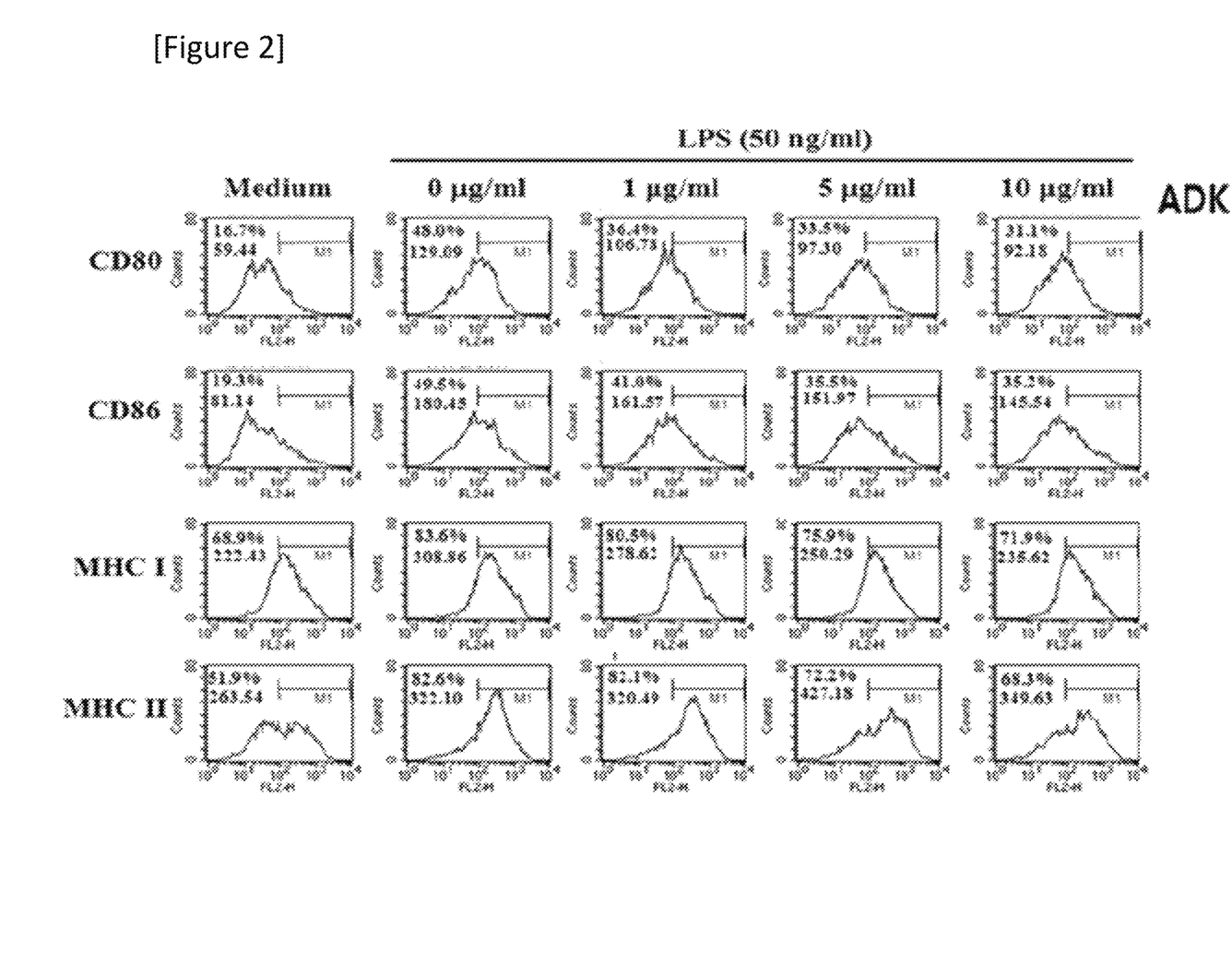
FIG. 2 is a diagram showing the expression levels of protein surface molecules, such as CD80, CD86, and MHC class I and II, in dendritic cells treated with ADK according to one exemplary embodiment of the present invention.

As shown in FIG. 2, it was revealed that, when the dendritic cells were treated with ADK and LPS, the expression of the co-stimulatory factors, such as CD80, CD86, MHC class I, and MHC class II, increased by LPS was reduced with an increasing concentration of ADK.

Example 3: Analysis of Effect of ADK on Secretion of Cytokines in Dendritic Cells To determine an effect of ADK on secretion of cytokines in dendritic cells, this experiment was performed, as follows. The dendritic cells were pre-treated with ADK at a concentration of 1, 5 or 10 μg/ml for an hour, treated with LPS at a concentration of 50 ng/ml for 24 hours, and the culture broth was recovered. Thereafter, the secretion levels of cytokines (TNF-α, IL-6, IL-1β, and IL-12 p70) were measured from the recovered culture broth using ELISA. The results are shown in FIG. 3.

Figure 3:
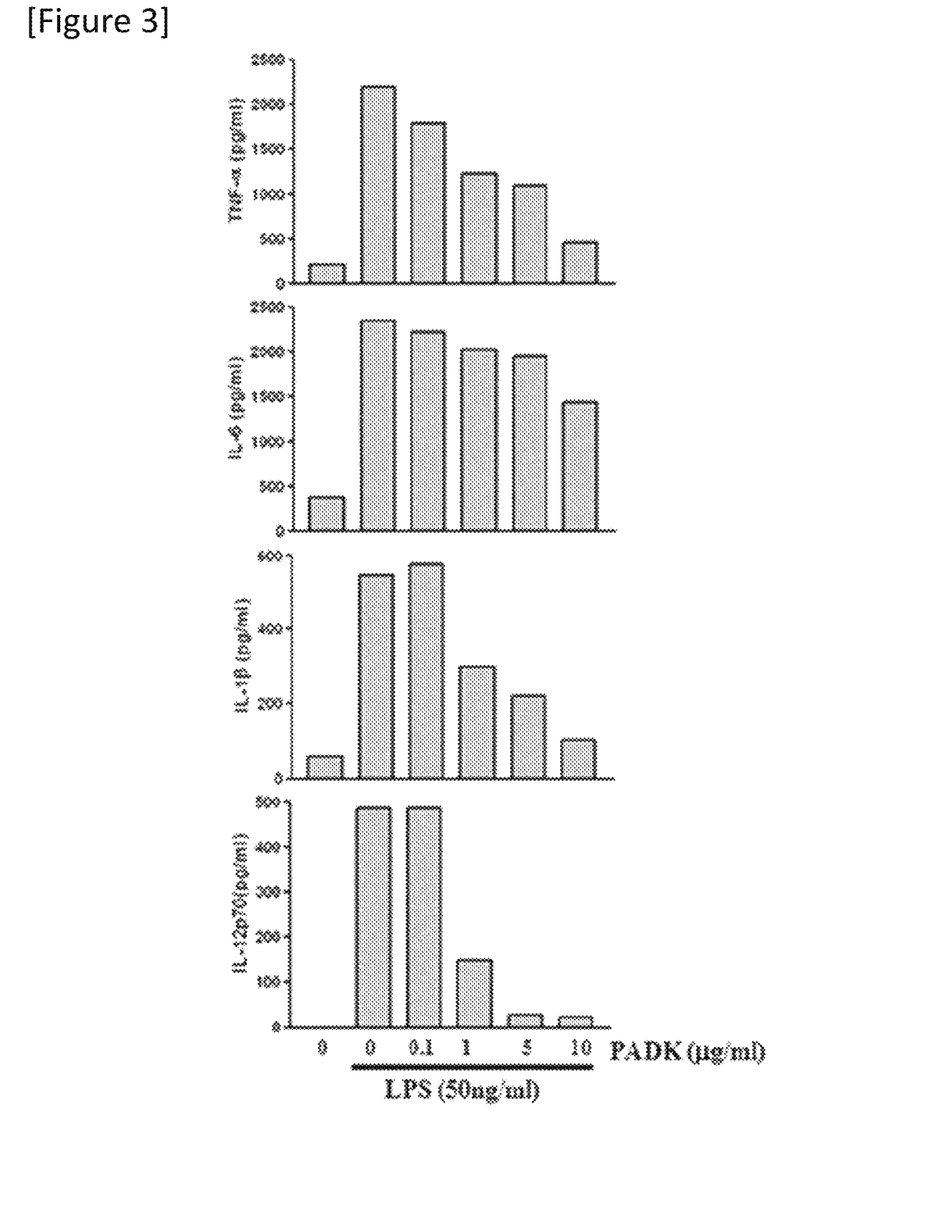
FIG. 3 is a diagram showing the secretion levels of cytokines (TNF-α, IL-6, IL-1β, and IL-12 p70) in dendritic cells treated with ADK according to one exemplary embodiment of the present invention.

As shown in FIG. 3, it was revealed that the secretion of the cytokines increased by LPS was reduced with an increasing concentration of ADK used for pretreatment of the dendritic cells.

Example 4: Analysis of Effect of ADK on Endocytic Activities of Dendritic Cells To determine an effect of ADK on the endocytic activities of dendritic cells, this experiment was performed, as follows. The dendritic cells were pre-treated with ADK at a concentration of 10 μg/ml for an hour, and then treated with LPS at a concentration of 50 ng/ml for 24 hours. Thereafter, 1 μg/ml of fluorescein-conjugated dextran (having a molecular weight of 40,000; Molecular Probes, Eugene, Oreg.) was added to the cultured dendritic cells for an hour. The dendritic cells were cultured respectively at 37° C. and 4° C. for 30 minutes, and the reaction was stopped by adding a cold staining buffer to the culture medium. Then, the dendritic cells were washed, and stained with phycoerythrin (PE)-conjugated CD11c (BD bioscience). Subsequently, the endocytic activities of dendritic cells for dextran-fluorescein isothiocyanate (FITC) were measured using a flow cytometer. The results are shown in FIG. 4.

Figure 4:
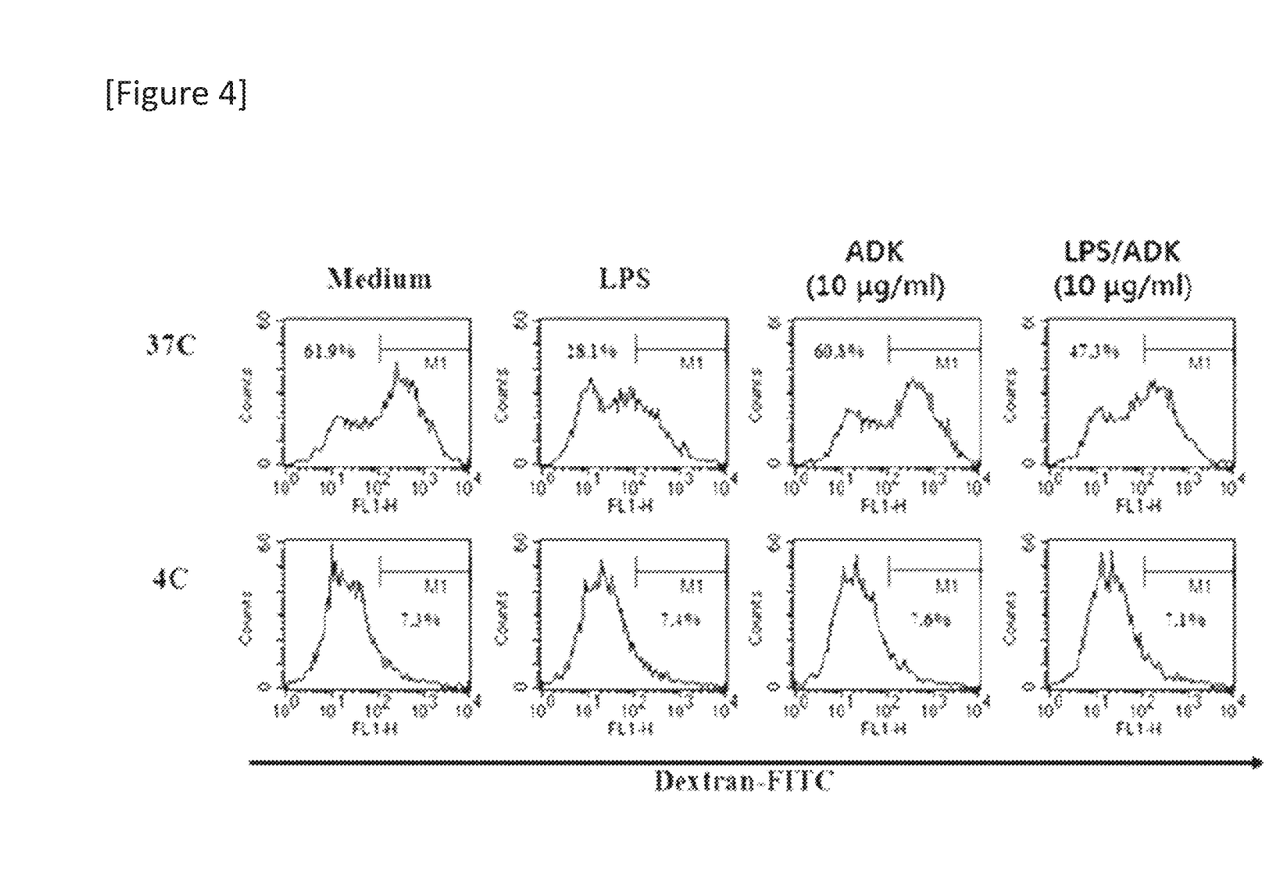
FIG. 4 is a diagram showing the results obtained by measuring ability to uptake dextran in dendritic cells treated with ADK according to one exemplary embodiment of the present invention.

As shown in FIG. 4, it was revealed that the endocytic activities for dextran was lowered when the dendritic cells were treated with LPS alone, while the endocytic activities for dextran lowered by LPS was enhanced when the dendritic cells were pre-treated with ADK. From these facts, it was confirmed that ADK inhibited a level of maturation of the dendritic cells by LPS.

Example 5: Analysis of Effect of ADK on TLR Agonists

To determine an effect of ADK on toll-like receptor (TLR) agonists, this experiment was performed, as follows. The dendritic cells were pre-treated with ADK at a concentration of 10 μg/ml for an hour, and treated with various TLR agonists for 24 hours, and the culture broths were recovered. The secretion levels of TNF-α were measured from the recovered culture broths using ELISA. The results are shown in FIG. 5.

Figure 5:
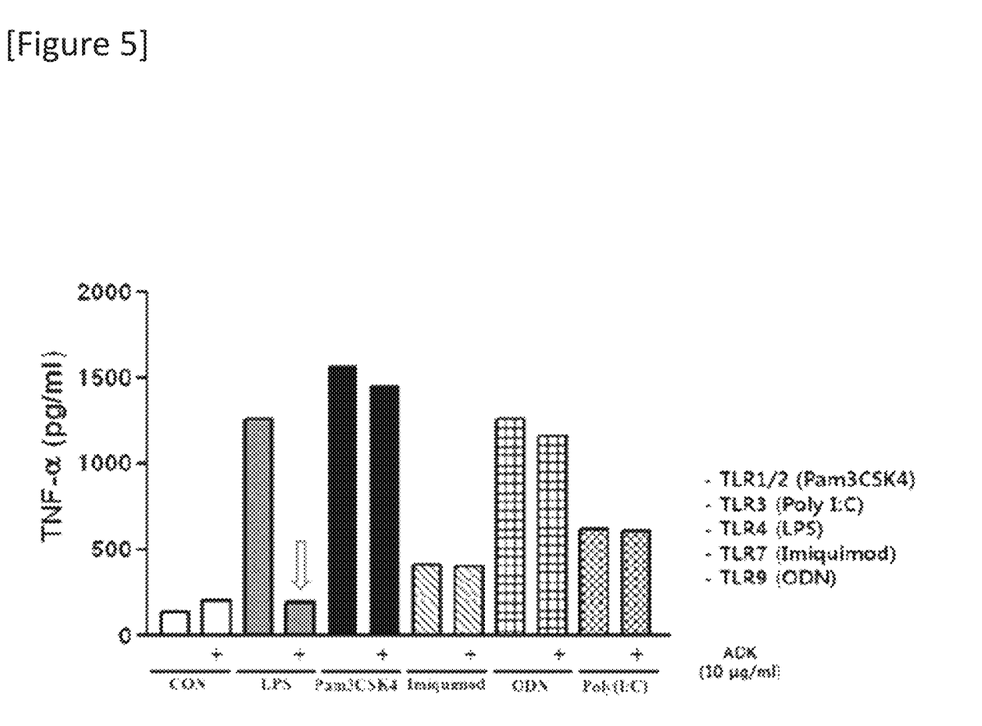
FIG. 5 is a diagram showing an effect of ADK on TLR agonists in dendritic cells according to one exemplary embodiment of the present invention.

As shown in FIG. 5, it was revealed that the secretion of TNF-α was remarkably reduced by pretreatment of ADK in a group treated with LPS which was a TLR4 agonist, while the other TLR agonists was not affected by the treatment of ADK. From these facts, it was confirmed that ADK specifically inhibited the signaling by TLR4.

Example 6: Analysis of Effect of ADK on Activities of Dendritic Cells by Means of LPS To determine an effect of ADK on the activities of dendritic cells by means of LPS, this experiment was performed, as follows. The dendritic cells were pre-treated with ADK, or an anti-ADK antibody at a concentration of 10 μg/ml for an hour, and treated with LPS at a concentration of 50 ng/ml for 24 hours, and the culture broth was recovered. The secretion level of TNF-α was measured from the recovered culture broth using ELISA. The results are shown in FIG. 6.

Figure 6:
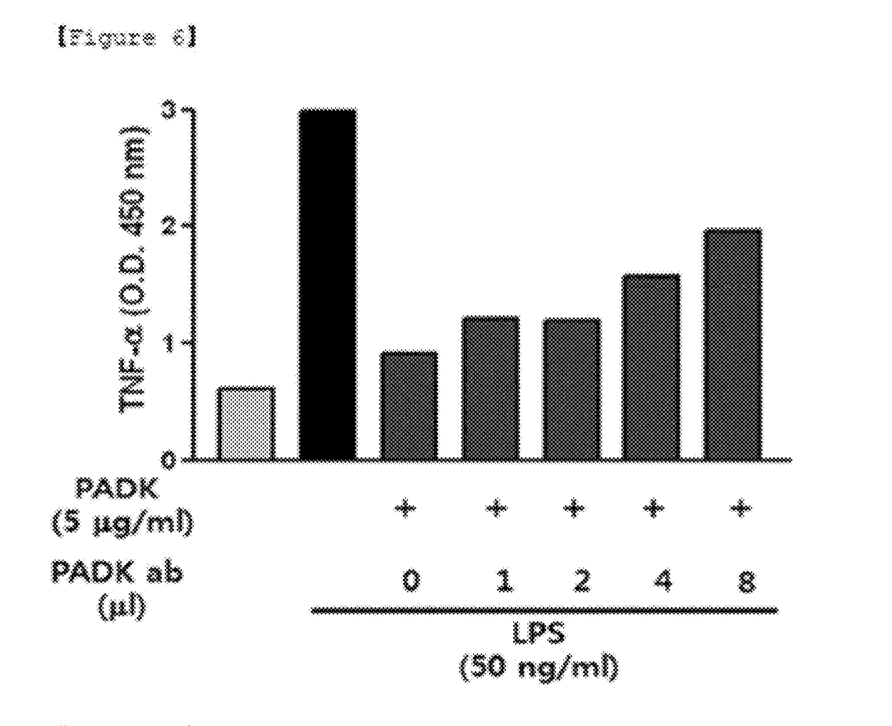
FIG. 6 is a diagram showing an effect of ADK on secretion of INF-α induced by LPS in dendritic cells according to one exemplary embodiment of the present invention.

As shown in FIG. 6, it was revealed that the secretion of TNF-α by LPS was inhibited when the dendritic cells were pre-treated with ADK, but the secretion of TNF-α was again enhanced when the dendritic cells were pre-treated together with ADK and the anti-ADK antibody.

Also, the dendritic cells were pre-treated with ADK at a concentration of 10 μg/ml for an hour, and treated with LPS at a concentration of 50 ng/ml for 0, 15, 30, or 60 minutes, and a total of proteins in the dendritic cells were recovered. The recovered proteins were subjected to Western blotting. The results are shown in FIG. 7.

Figure 7:
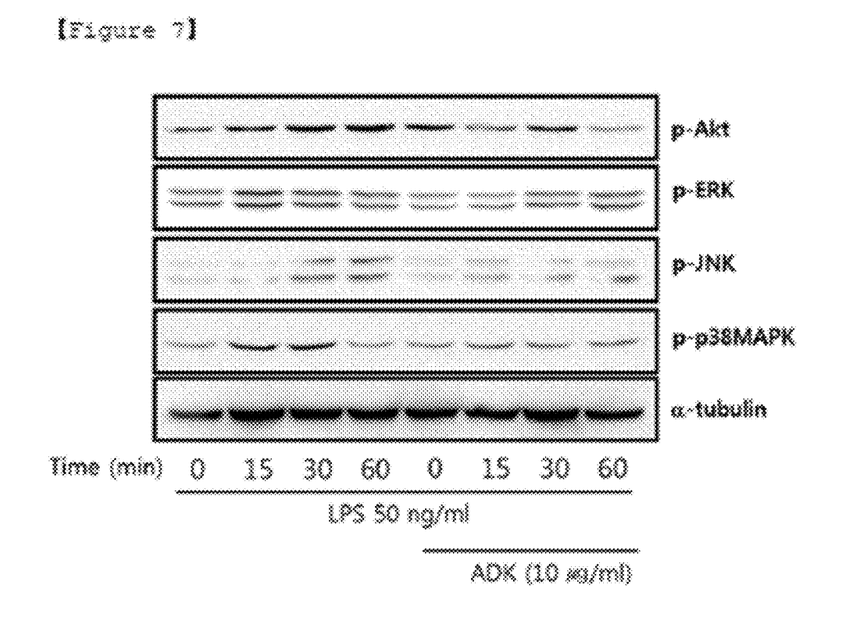
FIG. 7 is a diagram showing an effect of ADK on phosphorylation of AKT and MAPKs induced by LPS in dendritic cells according to one exemplary embodiment of the present invention.

As shown in FIG. 7, it was revealed that the phosphorylation levels of AKT and MAPKs activated by LPS were reduced when the dendritic cells were pre-treated with ADK.

From these experimental results, it was confirmed that ADK had an activity to inhibit the functions of LPS by binding to the LPS.

Example 7: Analysis of Interaction Between ADK and LPS

To analyze the interaction between ADK and LPS, this experiment was performed, as follows. The dendritic cells were treated with 100 μg of ADK and 0.5 mg of LPS for an hour. Thereafter, an immunoprecipitation method was performed using an anti-MS IgG or anti-LPS antibody, and Western blotting was performed using an anti-ADK antibody. The results are shown in FIG. 8.

Figure 8:
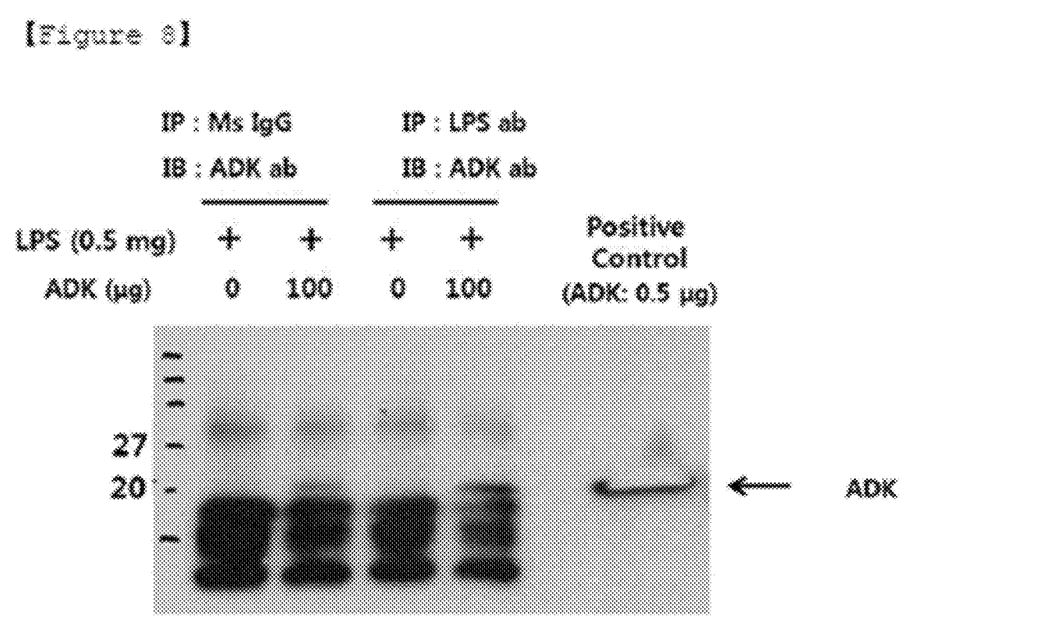
FIG. 8 is a diagram determining the interaction between ADK and LPS using immunoprecipitation and Western blotting according to one exemplary embodiment of the present invention.

As shown in FIG. 8, it was revealed that a band was present at a position corresponding to ADK having a molecular weight of approximately 20 kDa, indicating that ADK and LPS were bound to each other.

To verify the experimental results, the binding affinity and interaction between ADK and LPS were determined using Blitz equipment. More specifically, an anti-LPS antibody was bound to a Protein A sensor in the Blitz equipment in order to bind to the anti-LPS antibody, and washed with PBS in order to remove the unbound anti-LPS antibody in the sensor. LPS was bound to the sensor to which the anti-LPS antibody was bound, and the binding of ADK was analyzed (indicated by blue line). PBS was used as a negative control (indicated by black line). The results are shown in FIG. 9.

Figure 9:
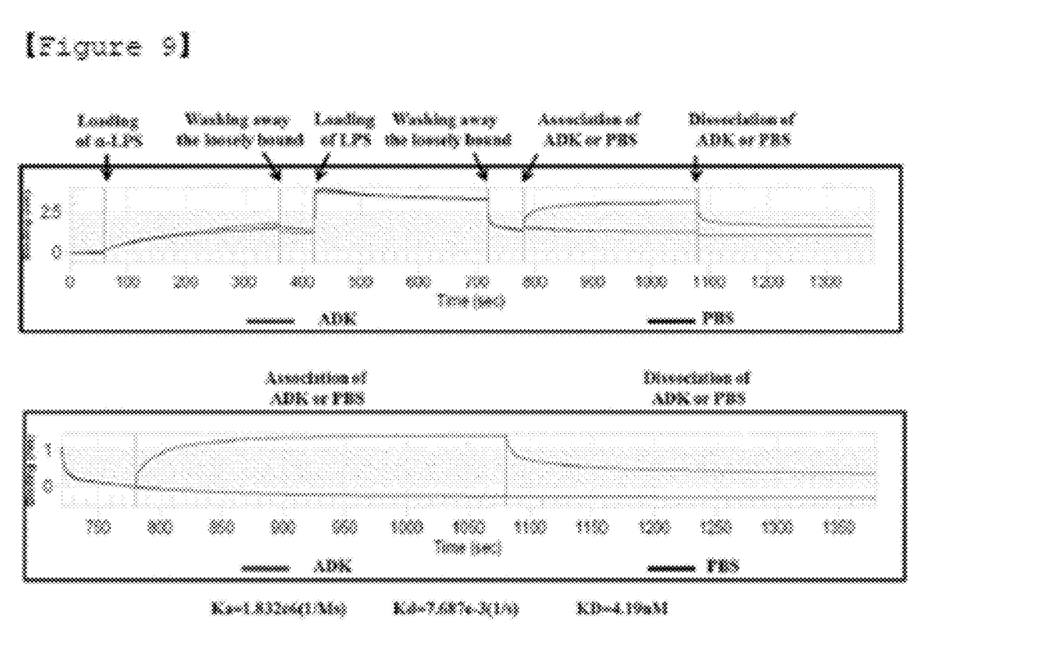
FIG. 9 is a diagram determining the interaction between ADK and LPS using Blitz equipment according to one exemplary embodiment of the present invention.

As shown in FIG. 9, it was revealed that the peak intensities were enhanced by the binding between LPS and ADK.

Example 8: Analysis of Therapeutic Effect of ADK in Sepsis Animal Model

To analyze a therapeutic effect of ADK in a sepsis animal model, this experiment was performed, as follows. Six-week old BALB/cAnNCriliOri mice were used in an animal model. The BALB/cAnNCriliOri mice were divided into an experimental group in which the mice were injected intra-abdominally with ADK (5 or 10 mg/kg) an hour before this experiment, and a control group, and then injected intra-abdominally with LPS (20 mg/kg) to induce sepsis. Thereafter, the viabilities of the mice with time were analyzed, and the sera were isolated at an hour after LPS administration to measure an amount of TNF-α in the sera. The results are shown in FIGS. 10 and 11.

Figure 10:
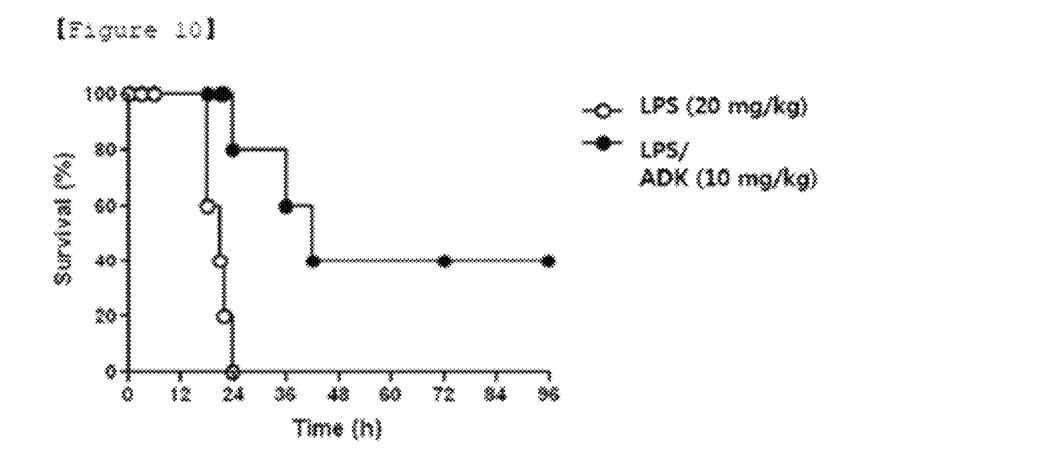
FIG. 10 is a diagram showing the viabilities of an ADK-administered group in a sepsis animal model according to one exemplary embodiment of the present invention.
Figure 11:
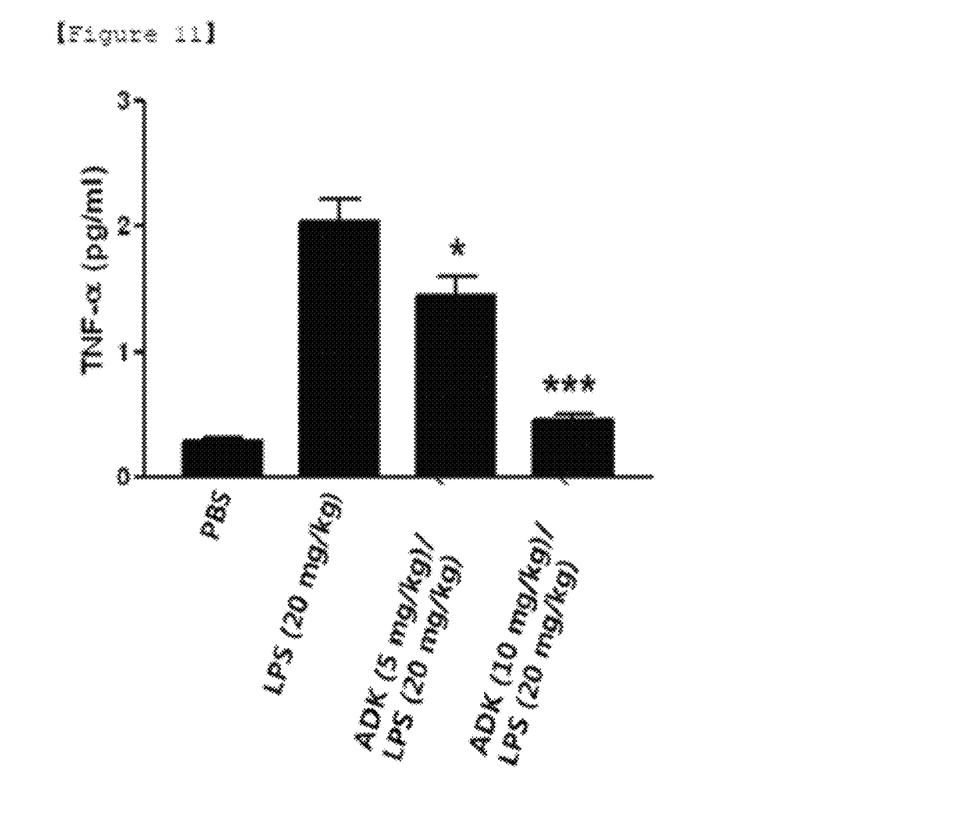
FIG. 11 is a diagram showing the INF-α levels in the serum of an ADK-administered group in a sepsis animal model according to one exemplary embodiment of the present invention.

As shown in FIG. 10, it was revealed that the viabilities of the mice remarkably increased in the case of the ADK-administered group in the sepsis animal model, compared to the control group. As shown in FIG. 11, it was also revealed that a level of the TNF-α in the sera of the mice increased by LPS was reduced in an ADK concentration-dependent manner.

Also, the mice were divided into an untreated group; an ADK (10 mg/kg) single-administered group; an LPS (10 mg/kg) single-administered group; and an ADK/LPS co-administered group in which ADK (10 mg/kg) was administered into the mice before an hour and LPS (10 mg/kg) was then administered into the mice. After 24 hours, the lungs and spleens were extracted from the mice of each group. The tissues of the lungs and spleens were embedded into paraffin sections, and stained with an H & E stain. Then, the spleen cells were isolated, and the death levels of B and T cells were analyzed using a flow cytometer. The results are shown in FIGS. 12 to 14.

Figure 12:
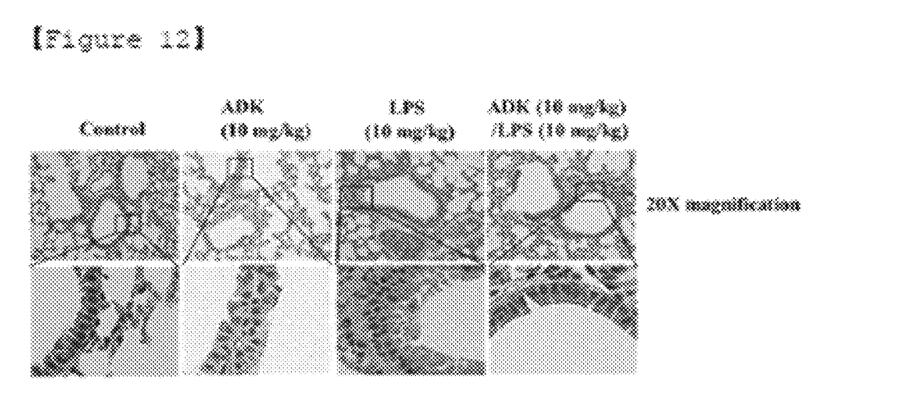
FIG. 12 is a diagram showing the infiltration levels of inflammatory cells in lung tissues of an ADK-administered group in a sepsis animal model according to one exemplary embodiment of the present invention.

As shown in FIG. 12, it was revealed that the infiltration of inflammatory cells was remarkably reduced in the lung tissues from the ADK-pretreated groups, compared to the lung tissues from the LPS single-administered group.

Figure 13:
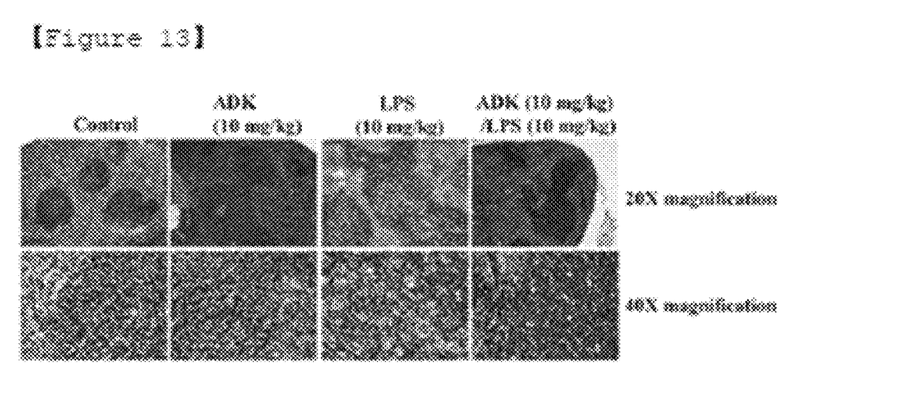
FIG. 13 is a diagram showing the levels of cell death in spleen tissue of an ADK-administered group in a sepsis animal model according to one exemplary embodiment of the present invention.

Also, as shown in FIG. 13, it was revealed that the cell death was remarkably reduced in the spleen tissues from the ADK-pretreated groups, compared to the spleen tissues from the LPS single-administered group (the shapes of the cells were irregular since the cell nuclei were destroyed upon the cell death).

Figure 14:
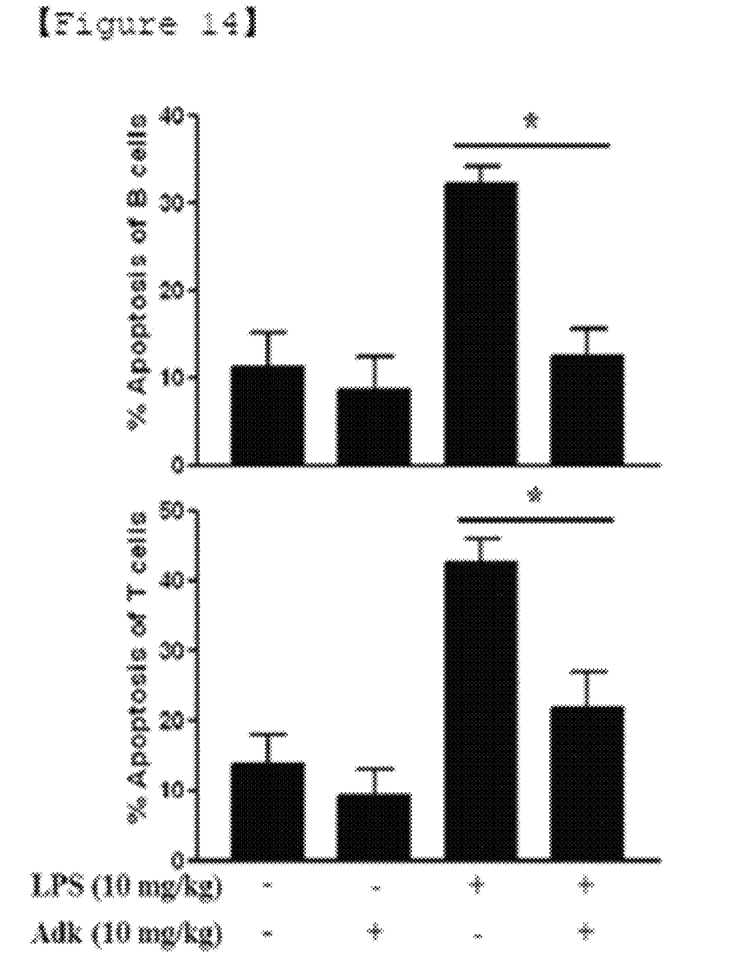
FIG. 14 is a diagram showing the levels of cell death of B and T cells in spleen cells of an ADK-administered group in a sepsis animal model according to one exemplary embodiment of the present invention.

Further, as shown in FIG. 14, it was revealed that the death of the B and T cells was remarkably reduced in the spleen cells from the ADK-pretreated groups, compared to the spleen cells from the LPS single-administered group.

From the experimental results as described above, it was confirmed that the ADK according to one exemplary embodiment of the present invention had an excellent therapeutic effect against sepsis.

Hereinafter, Preparation Examples of the pharmaceutical composition and the food composition according to one exemplary embodiment of the present invention will be described. However, it should be understood that detailed description is merely exemplary and illustrative of exemplary embodiments, and is not intended to limit the present invention.

Preparation Example 1: Preparation of Pharmaceutical Composition 1-1. Preparation of Powder

| | |
|---|---|
| ADK protein | 2 g |
| Lactose | 1 g |

A powder was prepared by mixing the above-described components and then filling the components into an airtight cloth.

1-2. Preparation of Tablet

| | |
|---|---|
| ADK protein | 100 mg |
| Corn starch | 100 mg |
| Lactose | 100 mg |
| Magnesium stearate | 2 mg |

The above-described components were mixed together, and a tablet was then prepared by formulating the components into a tablet according to a conventional method of preparing a tablet.

1-3. Preparation of Capsule

| | |
|---|---:|
| ADK protein | 100 mg |
| Corn starch | 100 mg |
| Lactose | 100 mg |
| Magnesium stearate | 2 mg |

The above-described components were mixed together, and a capsule was then prepared by filling the components into a gelatin capsule according to a conventional method of preparing a capsule.

Preparation Example 2: Preparation of Food Composition

2-1. Preparation of Health Food

| | |
|---|---:|
| ADK protein | 100 mg |
| Vitamin mixture | suitable amount |
| Vitamin A acetate | 70 g |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 g |
| Vitamin C | 10 mg |
| Biotin | 10 g |
| Nicotinamide | 1.7 mg |
| Folic acid | 50 g |
| Calcium pantothenate | 0.5 mg |
| Mineral blend | suitable amount |
| Ferrous sulfate | 1.75 mg |
| Zinc oxide | 0.82 mg |
| Magnesium carbonate | 25.3 mg |
| Monobasic potassium phosphate | 15 mg |
| Dibasic calcium phosphate | 55 mg |
| Potassium citrate | 90 mg |
| Calcium carbonate | 100 mg |
| Magnesium chloride | 24.8 mg |

The compositional ratios of the above-described vitamin and mineral blend were formed by blending relatively suitable components in the health food as described in the preferred Examples, but the blending ratios may optionally varied. Then, the above-described components were mixed according to a conventional method of preparing a health food to prepare a granule, which might be used to prepare a health food composition according to the conventional method.

The invention claimed is:

1. A method for preventing or treating sepsis or septic shock, the method comprising administering an adenylate kinase (ADK) protein as an active ingredient in a subject in need thereof, wherein the ADK protein comprises a protein at least 95% identical to the amino acid sequence set forth in SEQ ID NO: 1, wherein the sepsis or septic shock is caused by infection with *Staphylococcus* sp., *Streptococcus* sp., *Escherichia coli*, *Pseudomonas aeruginosa*, *Mycobacterium tuberculosis*, *Klebsiella pneumoniae*, eumycetes, and/or anaerobic bacteria.

2. The method of claim 1, wherein the ADK protein is derived from *Mycobacterium tuberculosis*.

3. The method of claim 1, wherein the ADK protein is encoded by the DNA sequence set forth in SEQ ID NO: 2.

4. The method of claim 1, wherein the ADK protein binds to a lipopolysaccharide (LPS).

* * * * *

SEQUENCE LISTING

<160> NUMBER OF SEQ ID NOS: 2

<210> SEQ ID NO 1
<211> LENGTH: 181
<212> TYPE: PRT
<213> ORGANISM: Mycobacterium tuberculosis

<400> SEQUENCE: 1

```
Met Arg Val Leu Leu Leu Gly Pro Pro Gly Ala Gly Lys Gly Thr Gln
1               5                   10                  15

Ala Val Lys Leu Ala Glu Lys Leu Gly Ile Pro Gln Ile Ser Thr Gly
            20                  25                  30

Glu Leu Phe Arg Arg Asn Ile Glu Gly Thr Lys Leu Gly Val Glu
        35                  40                  45

Ala Lys Arg Tyr Leu Asp Ala Gly Asp Leu Val Pro Ser Asp Leu Thr
    50                  55                  60

Asn Glu Leu Val Asp Asp Arg Leu Asn Asn Pro Asp Ala Ala Asn Gly
65                  70                  75                  80

Phe Ile Leu Asp Gly Tyr Pro Arg Ser Val Glu Gln Ala Lys Ala Leu
                85                  90                  95

His Glu Met Leu Glu Arg Arg Gly Thr Asp Ile Asp Ala Val Leu Glu
            100                 105                 110

Phe Arg Val Ser Glu Glu Val Leu Leu Glu Arg Leu Lys Gly Arg Gly
        115                 120                 125

Arg Ala Asp Asp Thr Asp Asp Val Ile Leu Asn Arg Met Lys Val Tyr
    130                 135                 140

Arg Asp Glu Thr Ala Pro Leu Leu Glu Tyr Tyr Arg Asp Gln Leu Lys
145                 150                 155                 160

Thr Val Asp Ala Val Gly Thr Met Asp Glu Val Phe Ala Arg Ala Leu
                165                 170                 175

Arg Ala Leu Gly Lys
            180
```

```
<210> SEQ ID NO 2
<211> LENGTH: 546
<212> TYPE: DNA
<213> ORGANISM: Mycobacterium tuberculosis

<400> SEQUENCE: 2
gtgagagttt tgttgctggg accgcccggg gcgggcaagg ggacgcaggc ggtgaagctg      60
gccgagaagc tcgggatccc gcagatctcc accggcgaac tcttccggcg caacatcgaa     120
gagggcacca agctcggcgt ggaagccaaa cgctacttgg atgccggtga cttggtgccg     180
tccgacttga ccaatgaact cgtcgacgac cggctgaaca atccggacgc ggccaacgga     240
ttcatcttgg atggctatcc acgctcggtc gagcaggcca aggcgcttca cgagatgctc     300
gaacgccggg ggaccgacat cgacgcggtg ctggagtttc gtgtgtccga ggaggtgttg     360
ttggagcgac tcaaggggcg tggccgcgcc gacgacaccg acgacgtcat cctcaaccgg     420
atgaaggtct accgcgacga gaccgcgccg ctgctggagt actaccgcga ccaattgaag     480
accgtcgacg ccgtcggcac catggacgag gtgttcgccc gtgcgttgcg ggctctggga     540
aagtag                                                                546
```